United States Patent
Gravelle et al.

(10) Patent No.: US 10,369,136 B2
(45) Date of Patent: Aug. 6, 2019

(54) POLYMORPHIC FORMS AND PROCESS

(71) Applicant: GALECTO BIOTECH AB, Copenhagen (DK)

(72) Inventors: Lise Gravelle, Laval (CA); Anders Pedersen, Lyngby (DK)

(73) Assignee: GALECTO BIOTECH AB, Copenhagen (DK)

( * ) Notice: Subject to any disclaimer, the term of this patent is extended or adjusted under 35 U.S.C. 154(b) by 0 days.

(21) Appl. No.: 16/062,206

(22) PCT Filed: Dec. 16, 2016

(86) PCT No.: PCT/EP2016/081432
§ 371 (c)(1),
(2) Date: Jun. 14, 2018

(87) PCT Pub. No.: WO2017/103109
PCT Pub. Date: Jun. 22, 2017

(65) Prior Publication Data
US 2018/0369208 A1 Dec. 27, 2018

(30) Foreign Application Priority Data

Dec. 18, 2015 (EP) ..................................... 15201223

(51) Int. Cl.
| | | |
|---|---|---|
| *A61K 31/4192* | (2006.01) | |
| *A61K 31/70* | (2006.01) | |
| *A61K 31/35* | (2006.01) | |
| *A61K 9/00* | (2006.01) | |
| *A61P 11/00* | (2006.01) | |
| *A61P 9/00* | (2006.01) | |
| *C07H 19/056* | (2006.01) | |
| *C07H 1/00* | (2006.01) | |

(52) U.S. Cl.
CPC ........ *A61K 31/4192* (2013.01); *A61K 9/0073* (2013.01); *A61K 31/35* (2013.01); *A61K 31/70* (2013.01); *A61P 9/00* (2018.01); *A61P 11/00* (2018.01); *C07H 1/00* (2013.01); *C07H 19/056* (2013.01)

(58) Field of Classification Search
None
See application file for complete search history.

(56) References Cited

U.S. PATENT DOCUMENTS

| | | |
|---|---|---|
| 5,458,135 A | 10/1995 | Patton et al. |
| 6,065,472 A | 5/2000 | Anderson et al. |
| 2004/0089295 A1 | 5/2004 | Gallem et al. |
| 2005/0056274 A1 | 3/2005 | Kunschir |
| 2006/0054166 A1 | 3/2006 | Knoch et al. |
| 2006/0097068 A1 | 5/2006 | Urich et al. |
| 2006/0102172 A1 | 5/2006 | Feiner et al. |
| 2008/0060640 A1 | 3/2008 | Waldner et al. |
| 2011/0155768 A1 | 6/2011 | Urich et al. |
| 2012/0167877 A1 | 7/2012 | Pumm et al. |

FOREIGN PATENT DOCUMENTS

WO 2014067986 A1 5/2014

OTHER PUBLICATIONS

Alison C. MacKinnon et al: "Regulation of Transforming Growth Factor-[beta]1-driven Lung Fibrosis by Galectin-3", American Journal of Respiratory and Critical Care Medicine, vol. 185, No. 5, Mar. 1, 2012 (Mar. 1, 2012), pp. 537-546.
International Search Report and Written Opinion dated Jan. 26, 2017 of corresponding application No. PCT/EP2016/081432, 9 pgs.
U.S. Office Action dated Feb. 4, 2019, in connection with corresponding U.S. Appl. No. 16/202,487 (13 pgs.).

*Primary Examiner* — Kamal A Saeed
(74) *Attorney, Agent, or Firm* — Maier & Maier, PLLC

(57) ABSTRACT

The present invention relates to a polymorph of a compound of formula (I)

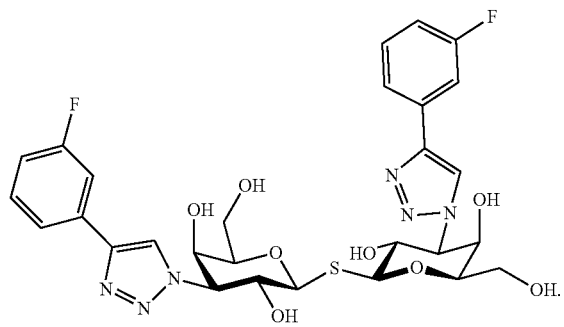

This polymorph is particularly suitable in treating IPF by pulmonary administration.

16 Claims, 11 Drawing Sheets

COUNTS

POSITION [°2Theta](Copper (Cu))

| Solvent | Temperature cycling | Crash cool (2°C) | Crash Cool (-20°C) | Anti-solvent addition | Evaporation | | |
|---|---|---|---|---|---|---|---|
| Acetone | | | | | | | Form 1 |
| Acetone:Water (20%) | | PLM | PLM | | | | Form 2 |
| Acetonitrile | | WD | | PLM | PLM | | Form 3 |
| Dichloromethane | | | | | PLM | | Form 4 |
| Diisopropyl ether | | | | | Am | | Form 5 |
| Dimethylacetamide | | | | | Am | | Form 6 |
| Dimethylformamide | | Am | PLM | | | | No solid |
| Dimethylsulfoxide | WD | Frozen | Frozen | PLM | Gum | Am | Amorphous by PLM |
| 1,4-Dioxane | Am | Frozen | Frozen | | PLM | PLM | Crystalline by PLM |
| Ethanol | | | | | WD | WD | Weak data (crystalline) |
| Ethyl acetate | | | | | WD | Gum | Gum |
| Hexane | | | | | Am | | Experiment not performed |
| Isopropyl acetate | | | | | PLM | | |
| Methanol | | | | | | | |
| Methylethyl ketone | | | | | WD | | |
| Methyl isobutyl ketone | | | | | PLM | | |
| N-methyl 2-pyrrolidone | | PLM | | | Gum | | |
| 2-Propanol | | | | | PLM | | |
| Tert-buytlmethyl ether | | | | | Am | | |
| Tetrahydrofuran | | | PLM | | Am | | |
| Toluene | | | | | Am | | |
| Water | WD | | Frozen | | PLM | | |
| Water:Propylene glycol (75:25) | WD | | Frozen | | | | |
| Water:PEG400:Ethanol (65:25:10) | WD | | Frozen | | Gum | | |

FIG. 11

POLYMORPHIC FORMS AND PROCESS

TECHNICAL FIELD

The present invention relates to a polymorph of 3,3'-Dideoxy-3,3'-bis-[4-(3-fluorophenyl)-1H-1,2,3-triazol-1-yl]-1,1'-sulfanediyl-di-β-D-galactopyranoside.

BACKGROUND ART

Idiopathic pulmonary fibrosis (IPF) represents a massive worldwide health burden. It is a chronic condition of unknown etiology in which repeated acute lung injury causes progressive fibrosis resulting in destruction of lung architecture, deteriorating lung function with consequent respiratory failure and death. Although idiopathic pulmonary fibrosis (IPF) is the archetypal and most common cause of lung fibrosis, numerous respiratory diseases can progress to pulmonary fibrosis, and this usually signifies a worse prognosis. The median time to death from diagnosis is 2.5 years and the incidence and prevalence of IPF continues to rise. It remains one of the few respiratory conditions for which there are no effective therapies, and there are no reliable biomarkers to predict disease progression. The mechanisms resulting in pulmonary fibrosis are unclear but centre around aberrant wound healing as a consequence of repetitive epithelial injury from an as yet unknown cause. IPF is characterized by fibroblastic foci containing fibroblasts/myofibroblasts which show increased activation response to fibrogenic cytokines such as transforming growth factor-ß1 (TGF-ß1). There is a big unmet need for drugs for treatment of Idiopathic pulmonary fibrosis.

SUMMARY OF THE DISCLOSURE 3,3'-Dideoxy-3,3'-bis-[4-(3-fluorophenyl)-1H-1,2,3-triazol-1-yl]-1,1'-sulfanediyl-diβ-D-galactopyranoside is a white to off white crystalline solid where 6 polymorphs as well as an amorphous form have been identified.

In one aspect, the present invention relates to a polymorph of a compound of formula (I)

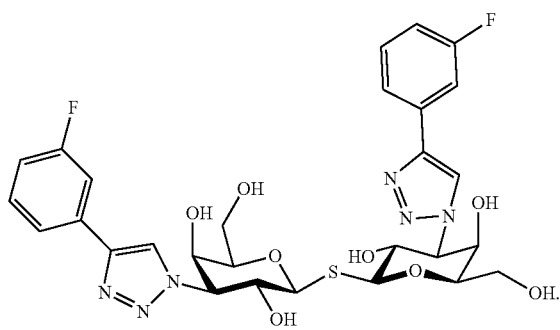

The compound of formula (I) is 3,3'-Dideoxy-3,3'-bis-[4-(3-fluorophenyl)-1H-1,2,3-triazol-1-yl]-1,1'-sulfanediyl-di-β-D-galactopyranoside and has the polymorphic Form 1 as identified in the XRPD diffractogram peak list

| No. | Pos. [° 2Th.] | Rel. Int. [%] |
|---|---|---|
| 1 | 7.1269 | 77.72 |
| 2 | 7.5067 | 56 |
| 3 | 10.125 | 36.86 |
| 4 | 14.3791 | 32.28 |
| 5 | 15.0846 | 18.59 |
| 6 | 15.8201 | 35.78 |
| 7 | 16.7088 | 78.1 |
| 8 | 18.6001 | 21.29 |
| 9 | 19.7777 | 100 |
| 10 | 20.3353 | 57.04 |
| 11 | 21.7744 | 79.92 |
| 12 | 22.6053 | 35.8 |
| 13 | 23.4305 | 45.78 |
| 14 | 24.3658 | 51.03 |
| 15 | 25.8091 | 54.36 |
| 16 | 26.7046 | 25.38 |
| 17 | 29.028 | 16.19 |
| 18 | 30.2989 | 28.02 |
| 19 | 32.2693 | 14.86 |
| 20 | 33.5132 | 11.55 |
| 21 | 34.6078 | 11.54 |
| 22 | 35.8435 | 9.6 |
| 23 | 44.6257 | 22.73 |

Moreover, the polymorphic form 1 of 3,3'-Dideoxy-3,3'-bis-[4-(3-fluorophenyl)-1H-1,2,3-triazol-1-yl]-1,1'-sulfanediyl-di-β-D-galactopyranoside can be identified in the XRPD diffractogram in FIG. 1 or FIG. 2.

In a further aspect of the present invention a polymorph of 3,3'-Dideoxy-3,3'-bis-[4-(3-fluorophenyl)-1H-1,2,3-triazol-1-yl]-1,1'-sulfanediyl-di-β-D-galactopyranoside is designated Form 1 and is a hydrated crystalline form. The hydrate is not stoichiometric but rather a channel hydrate. Form 1 is dried upon synthesis, however it will pick up moisture and equilibrate at around 3-5% water content. Form 1 is stable and does not convert to the other forms over time. Furthermore, form 1 can be further processed by micronization, which is particularly useful when preparing a composition for use in dry powder delivery to the lungs, in particular the narrowest parts of the lung tissue that is the bronchioles and the alveoli.

In a further aspect, the present invention relates to a pharmaceutical composition comprising a polymorph of the present invention, and optionally a pharmaceutically acceptable additive.

In a still further aspect the present invention relates to a process of making a polymorph of the present invention comprising the steps of suspending or dissolving 3,3'-Dideoxy-3,3 '-bis-[4-(3-fluorophenyl)-1H-1,2,3-triazol-1-yl]-1,1'-sulfanediyl-di-β-D-galactopyranoside in an organic solvent and then making form 1 by temperature cycling, crash cooling or evaporation, or a combination thereof.

In a further aspect, the present invention relates to a process for preparing an amorphous form of a compound of formula (I)

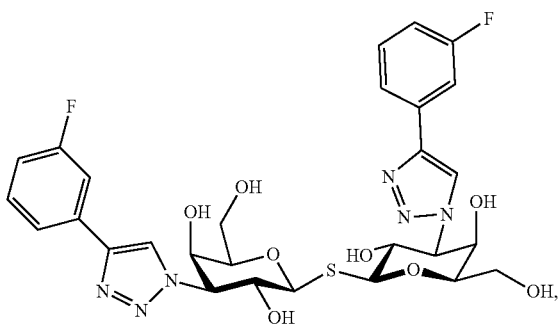

comprising the steps of spray drying a solution of 3,3'-Dideoxy-3,3'-bis-[4-(3-fluorophenyl)-1H-1,2,3-triazol-1-yl]-1,1'-sulfanediyl-di-β-D-galactopyranoside in an organic solvent and collecting the amorphous compound of formula (I).

In a still further aspect the present invention relates to a method for treatment of pulmonary fibrosis in a human comprising administering to the narrowest parts of the lung tissue of the human an amount of a polymorph of the present invention effective to treat said pulmonary fibrosis.

BRIEF DESCRIPTION OF FIGURES

FIG. 11: Conditions to generate 6 polymorphs of 3,3'-Dideoxy-3,3'-bis-[4-(3-fluorophenyl)-1H-1,2,3-triazol-1-yl]-1,1'-sulfanediyl-di-β-D-galactopyranoside.

DETAILED DESCRIPTION

The compound of formula (I) has the chemical name (IUPAC) 3,3'-Dideoxy-3,3'-bis[4-(3-fluorophenyl)-1H-1,2,3-triazol-1-yl]-1,1'-sulfanediyl-di-β-D-galactopyranoside.

The compound of formula (I) may be prepared as described in US2014/0121179 or WO2014/067986, wherein an amorphous solid is produced.

The present invention concerns a polymorph of a compound of formula (I)

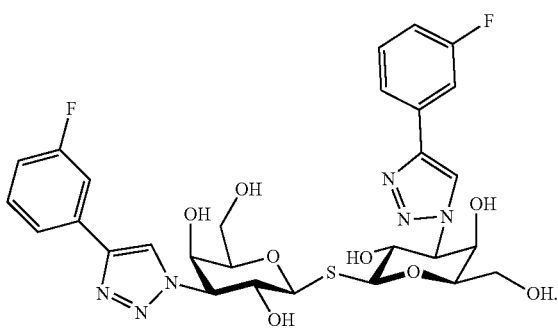

In one embodiment, the compound of formula (I) is 3,3'-Dideoxy-3,3'-bis-[4-(3-fluorophenyl)-1H-1,2,3-triazol-1-yl]-1,1'-sulfanediyl-di-β-D-galactopyranoside and has the polymorphic form 1 as identified in the XRPD diffractogram peak list

| No. | Pos. [° 2Th.] | Rel. Int. [%] |
|---|---|---|
| 1 | 7.1269 | 77.72 |
| 2 | 7.5067 | 56 |
| 3 | 10.125 | 36.86 |
| 4 | 14.3791 | 32.28 |
| 5 | 15.0846 | 18.59 |
| 6 | 15.8201 | 35.78 |
| 7 | 16.7088 | 78.1 |
| 8 | 18.6001 | 21.29 |
| 9 | 19.7777 | 100 |
| 10 | 20.3353 | 57.04 |
| 11 | 21.7744 | 79.92 |
| 12 | 22.6053 | 35.8 |
| 13 | 23.4305 | 45.78 |
| 14 | 24.3658 | 51.03 |
| 15 | 25.8091 | 54.36 |
| 16 | 26.7046 | 25.38 |
| 17 | 29.028 | 16.19 |
| 18 | 30.2989 | 28.02 |
| 19 | 32.2693 | 14.86 |
| 20 | 33.5132 | 11.55 |
| 21 | 34.6078 | 11.54 |
| 22 | 35.8435 | 9.6 |
| 23 | 44.6257 | 22.73 |

Figure 1:
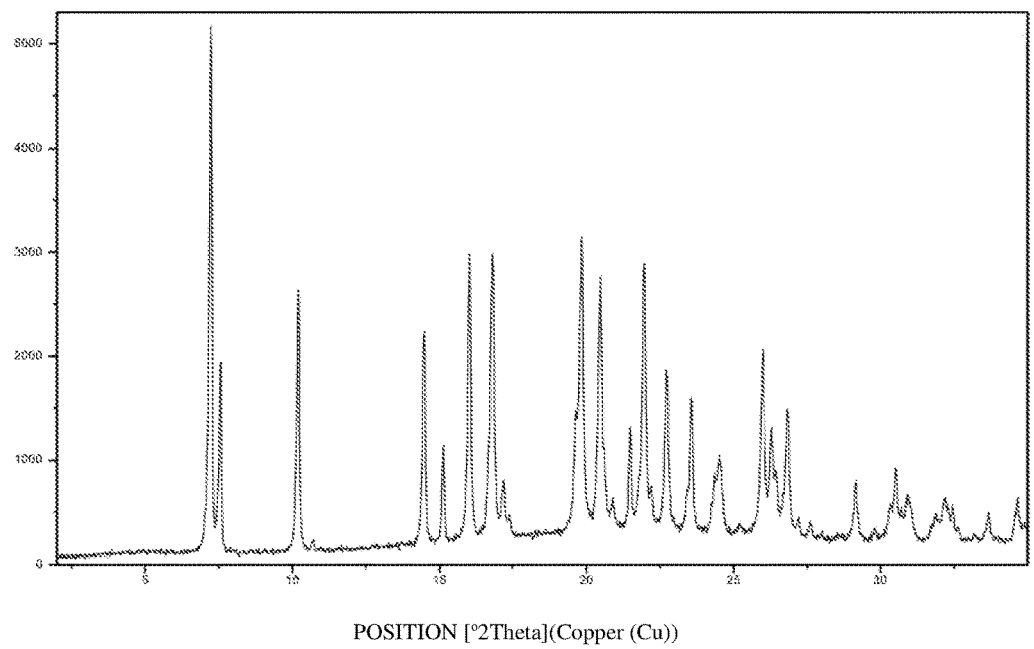
FIG. 1: XRPD Diffractogram for Form 1.

The compound of formula (I) is 3,3'-Dideoxy-3,3'-bis-[4-(3-fluorophenyl)-1H-1,2,3-triazol-1-yl]-1,1'-sulfanediyl-di-β-D-galactopyranoside and has the polymorphic form 1 as identified in the XRPD diffractogram in FIG. 1.

Figure 2:
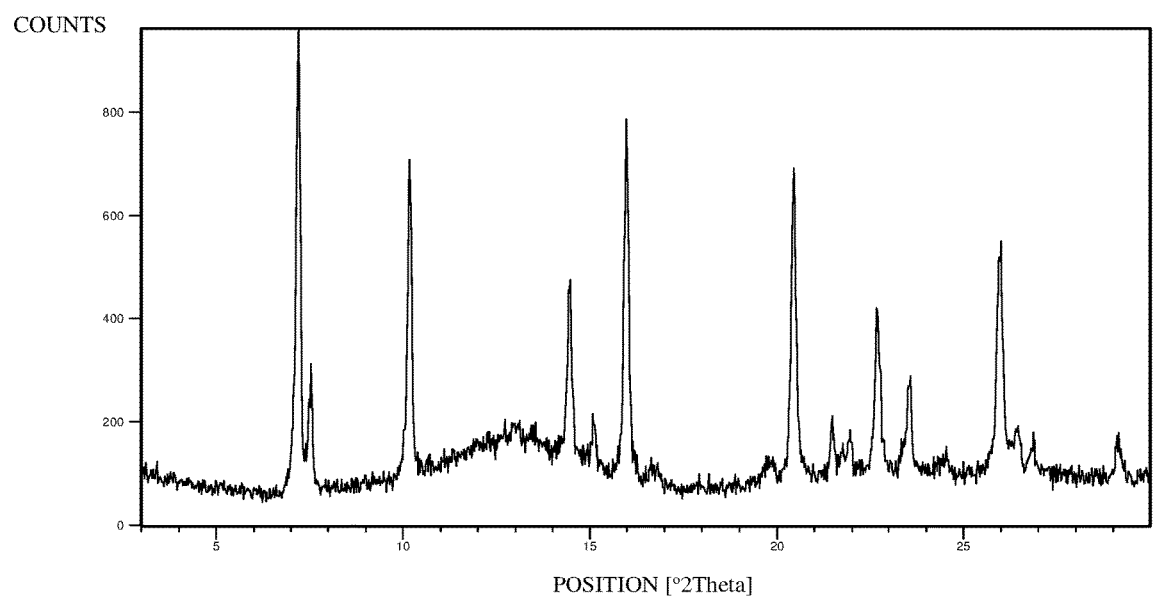
FIG. 2: XRPD Diffractogram for Form 1.
Figure 3:
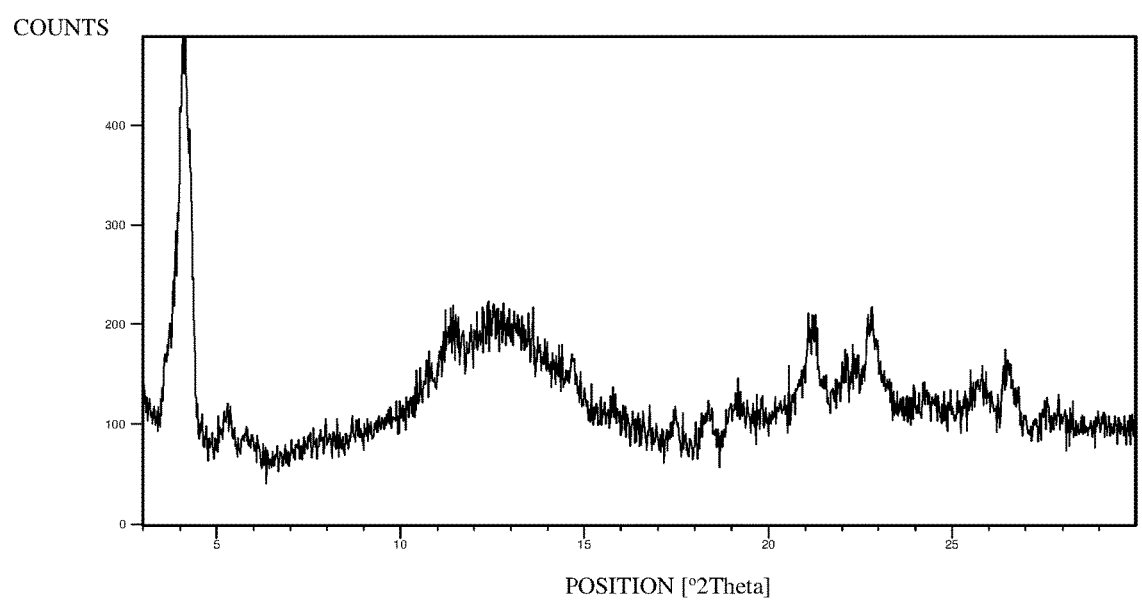
FIG. 3: XRPD Diffractogram for Form 2.
Figure 4:
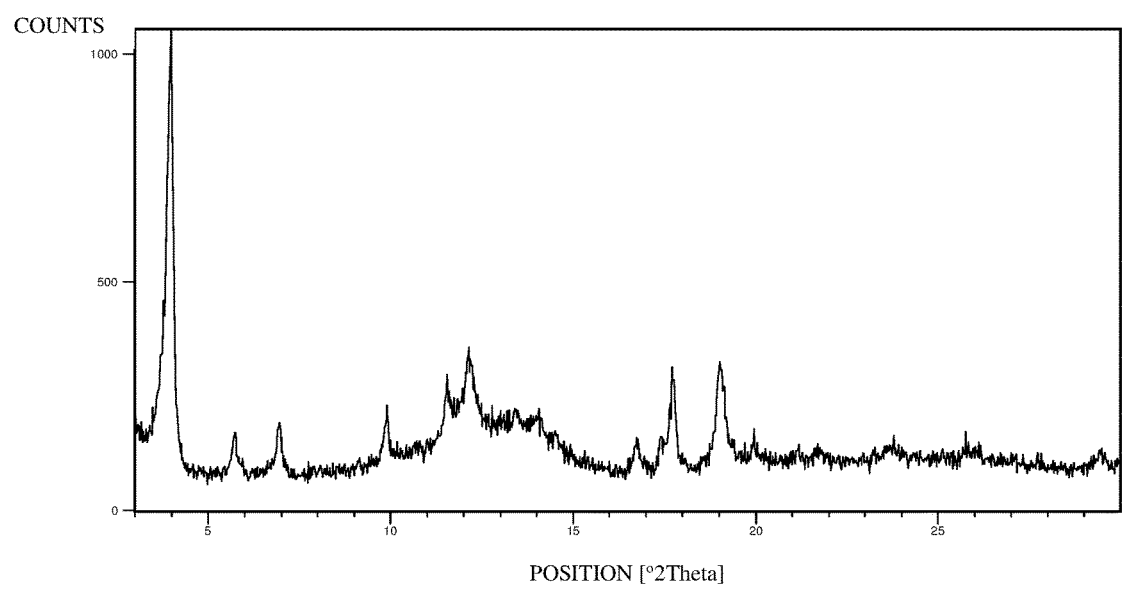
FIG. 4: XRPD Diffractogram for Form 3.
Figure 5:
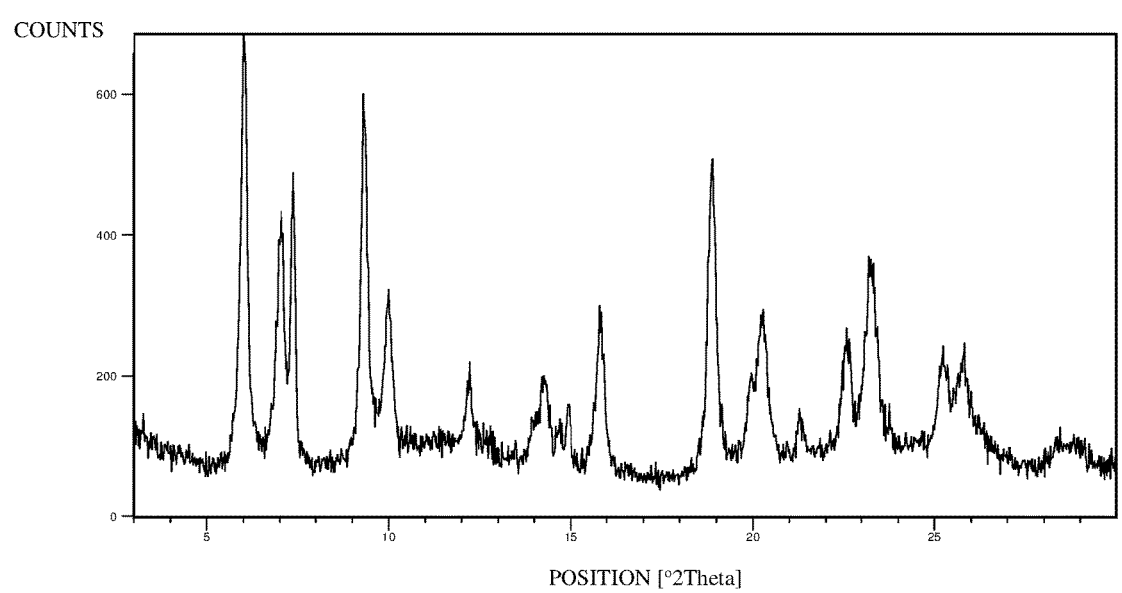
FIG. 5: XRPD Diffractogram for Form 4.
Figure 6:
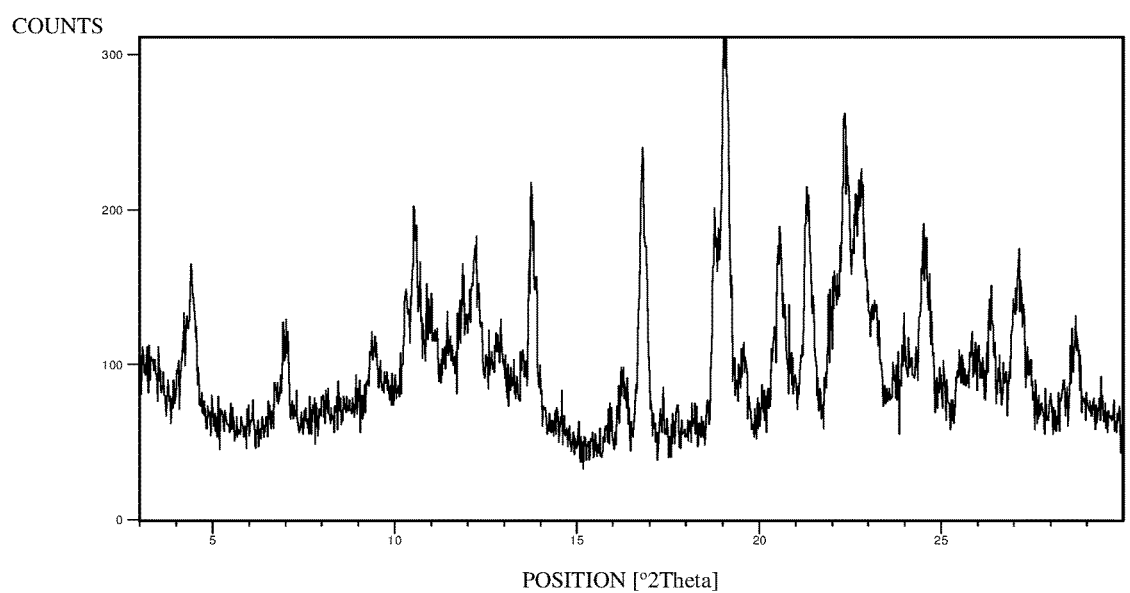
FIG. 6: XRPD Diffractogram for Form 5.
Figure 7:
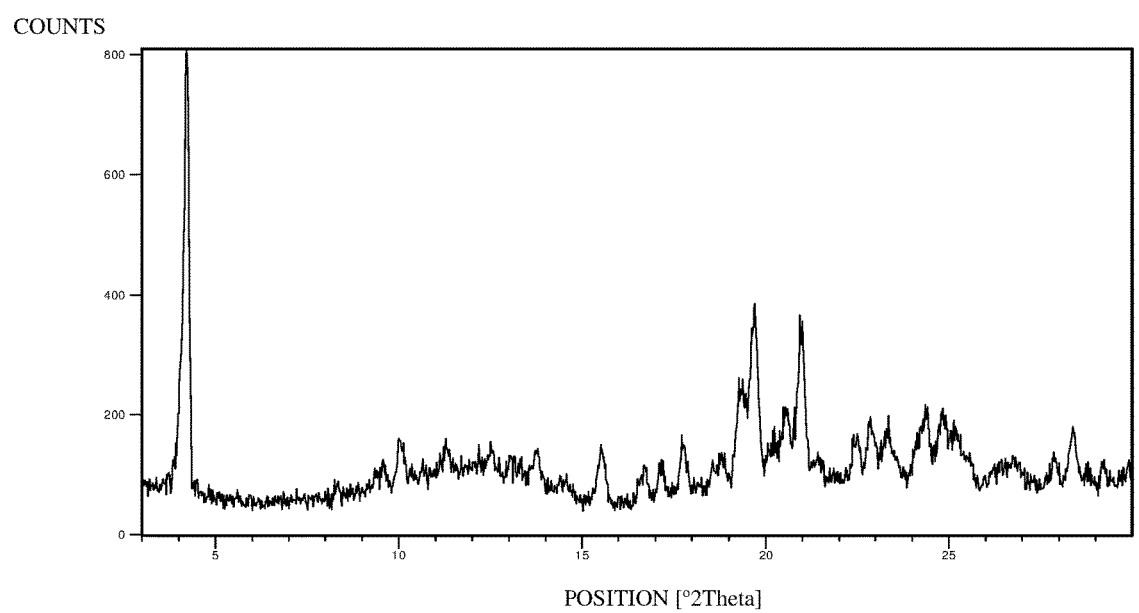
FIG. 7: XRPD Diffractogram for Form 6.

The compound of formula (I) is 3,3'-Dideoxy-3,3'-bis-[4-(3-fluorophenyl)-1H-1,2,3-triazol-1-yl]-1,1'-sulfanediyl-di-β-D-galactopyranoside and has the polymorphic form 1 as identified in the XRPD diffractogram in FIG. 2.

In a further embodiment, the compound of formula (I) is 3,3'-Dideoxy-3,3'-bis-[4-(3-fluorophenyl)-1H-1,2,3-triazol-1-yl]-1,1'-sulfanediyl-di-β-D-galactopyranoside as a hydrate.

In a still further embodiment the 3,3'-Dideoxy-3,3'-bis-[4-(3-fluorophenyl)-1H-1,2,3-triazol-1-yl]-1,1'-sulfanediyl-di-β-D-galactopyranoside hydrate contains 3-5% water (weight %).

In a further embodiment, the compound of formula (I) is 3,3'-Dideoxy-3,3'-bis-[4-(3-fluorophenyl)-1H-1,2,3-triazol-1-yl]-1,1'-sulfanediyl-di-β-D-galactopyranoside selected from Form 2, 3, 4, 5 or 6 as identified in the XRPD diffractogram in FIGS. 3-7, respectively. Form 5 (FIG. 6) is particularly interesting as it is stable and suitable for use in a nebulizer for pulmonary administration.

In a still further embodiment the polymorph is a dry powder, such as micronized polymorph. Such as, micronized Form 1.

In a further embodiment, the polymorph, such as Form 1, is micronized to a size that can reach the narrowest parts of the lung tissue of the human, such as the bronchioles and the alveoli.

In a further aspect, the present invention relates to a polymorph of the present invention for use in a method for treatment of pulmonary fibrosis in a human. Preferably the polymorph for use in treatment of pulmonary fibrosis is selected from Form 1 and 5, typically Form 1.

In a still further aspect the present invention relates to a pharmaceutical composition comprising the polymorph of the present invention, and optionally a pharmaceutically acceptable additive. Typically, the polymorph used in the composition is Form 1 as a dry powder, such as micronized dry powder neat or mixed with an additive, such as lactose.

In a further aspect, the present invention relates to a DPI comprising a polymorph of the present invention, such as form 1. In an embodiment, the polymorph, such as Form 1, is micronized to a size that can reach the narrowest parts of the lung tissue of the human, such as the bronchioles and the alveoli. In a further embodiment, the DPI comprising the polymorph of form 1 for use in a method for treatment of pulmonary fibrosis in a human. In a still further embodiment the DPI is a single or multiple dose DPI inhaler. In one particular embodiment, the dry powder inhaler is RS01 Monodose Dry Powder Inhaler (Plastiape).

Another aspect concerns a process of making a polymorph Form 1 of the present invention comprising the steps of suspending or dissolving 3,3'-Dideoxy-3,3'-bis-[4-(3-fluorophenyl)-1H-1,2,3-triazol-1-yl]-1,1'-sulfanediyl-di-β-D-galactopyranoside in an organic solvent and then making Form 1 by temperature cycling, crash cooling or evaporation, or a combination thereof. The compound 3,3'-Dideoxy-3,3'-bis-[4-(3-fluorophenyl)-1H-1,2,3-triazol-1-yl]-1,1'-sulfanediyl-di-β-D-galactopyranoside used as starting material may be amorphous or any crystalline form since the above process will generate Form 1. In a further embodiment, the organic solvent is selected from methanol, ethanol, acetone, acetonitrile, toluene, tert-butylmethylether, hexane and diisopropylether as well as mixtures thereof.

A further aspect concerns a process for preparing an amorphous form of a compound of formula (I)

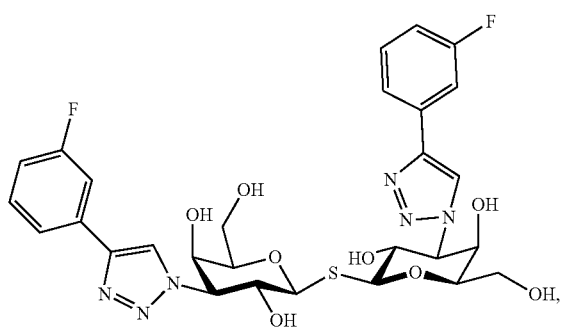

comprising the steps of spray drying a solution of 3,3'-Dideoxy-3,3'-bis-[4-(3-fluorophenyl)-1H-1,2,3-triazol-1-yl]-1,1'-sulfanediyl-di-β-D-galactopyranoside in an organic solvent and collecting the amorphous compound of formula (I). The compound 3,3'-Dideoxy-3,3'-bis-[4-(3-fluorophenyl)-1H-1,2,3-triazol-1-yl]-1,1'-sulfanediyl-di-β-D-galactopyranoside used as starting material may be any crystalline form since the above process will generate the amorphous form from the dissolved compound. In a further embodiment the organic solvent is selected from a mixture of acetone and water, such as acetone:water 50:50 to 80:20. In a still further embodiment the dissolved compound is introduced in a drying chamber at a feed concentration of from 0.5% to 20% by weigth, such as from 1-10% weight, such as from 2-7% weight, e.g. about 3.5% weight. In a further embodiment, the drying chamber has a drying gas temperature at the inlet of from 120-160° C., such as from 140-150° C., e.g. about 144° C. In a still further embodiment the drying chamber has a drying gas temperature at the outlet of from 60-90° C., such as from 70-80° C., e.g. about 75° C. In a further embodiment drying time in the drying chamber is from 30-120 minutes, such as from 45-75 minutes, e.g. about 50 minutes.

In a still further aspect the present invention relates to a method for treatment of pulmonary fibrosis in a human comprising administering to the narrowest parts of the lung tissue of the human an amount of a polymorph of the present invention, such as Form 1 or 5, effective to treat said pulmonary fibrosis.

In a further embodiment, the pulmonary fibrosis is Idiopathic pulmonary fibrosis (IPF).

In a further embodiment, the administration is carried out by a dry powder inhaler. Typically, a single or multiple dose DPI inhaler is used. In one particular embodiment, the dry powder inhaler is RS01 Monodose Dry Powder Inhaler (Plastiape).

When a polymorph of the compound of formula (I), typically Form 1, is formulated as a dry powder it may be present in a suitable particle size selected from a mean mass aerodynamic diameter (MMAD) between 0.1 and 20 μm, such as a MMAD between 0.5 and 10 μm, such as between 1 and 5 μm, typically between 2 and 3 μm. The selected ranges do not exclude the presence of particles sizes outside these ranges, but the selected ranges are those that provide the desired effect as described herein.

In a still further embodiment the narrowest parts of the lung tissue are the bronchioles and the alveoli.

In a further embodiment the once daily amount is from 0.15 mg to 50 mg, such as 0.15 mg to 0.50 mg, 0.50 mg to 0.75 mg, 0.75 mg to 1.25 mg, 1.25 mg to 1.5 mg, 1.5 mg to 1.75 mg, 1.75 mg to 2 mg, 2 mg to 2.25 mg, 2.25 mg to 2.5 mg, 2.5 mg to 2.75 mg, 2.75 mg to 3 mg, 3 mg to 5 mg, 5 mg to 7 mg, 7 mg to 8 mg, 8 mg to 10 mg, 10 mg to 20 mg and 20 mg to 50 mg. The once daily amount form 1.5 mg to 20 mg result in a concentration of the active compound of formula (I) in BAL fluids or macrophages or both of from 1 nM to 500 μM. In particular, the once daily amount form 1.5 mg to 20 mg result in a concentration of the active compound of formula (I) in BAL fluids or macrophages or both of from 1 nM to 100 μM. More preferred concentrations of from 10 nM to 10 μM or more preferred 100 nM to 1 μM can be provided with once daily amount from 1 mg to 10 mg, such as from 1 mg to 3 mg or 3 mg to 10 mg, e.g. 1 mg to 3 mg. Other preferred concentrations of the active compound of formula (I) in BAL fluids is from 10 nM to 10 μM, such as from 100 nM to 10 μM, typically from 500 nM to 10 μM, such as up to 4 μM. Other preferred concentrations of the active compound of formula (I) in macrophages is from 1 μM to 500 μM, such as from 10 μM to 250 μM, typically from 50 μM to 200 μM, such as up to 100 μM.

In a still further embodiment the treatment is chronic treatment.

The term "treatment" and "treating" as used herein means the management and care of a patient for the purpose of combating a condition, such as a disease or a disorder. The term is intended to include the full spectrum of treatments for a given condition from which the patient is suffering, such as administration of the active compound to alleviate the symptoms or complications, to delay the progression of the disease, disorder or condition, to alleviate or relief the symptoms and complications, and/or to cure or eliminate the disease, disorder or condition as well as to prevent the condition, wherein prevention is to be understood as the management and care of a patient for the purpose of combating the disease, condition, or disorder and includes the administration of the active compounds to prevent the onset of the symptoms or complications. The treatment is performed in a chronic way. The patient to be treated is a human subject diagnosed with pulmonary fibrosis or other types of lung fibrosis.

The term "an amount effective to treat pulmonary fibrosis" of a compound of formula (I) of the present invention as used herein means an amount sufficient to cure, alleviate or partially arrest the clinical manifestations of pulmonary fibrosis and its complications. Effective amounts for each purpose will depend on the severity of the disease or injury as well as the weight and general state of the subject. It will be understood that determining an appropriate dosage may be achieved using routine experimentation, by constructing a matrix of values and testing different points in the matrix, which is all within the ordinary skills of a trained physician or veterinary.

As used herein "pharmaceutically acceptable additive" is intended without limitation to include carriers, excipients, diluents, adjuvant, colorings, aroma, preservatives etc. that the skilled person would consider using when formulating a compound of the present invention in order to make a pharmaceutical composition.

The adjuvants, diluents, excipients and/or carriers that may be used in the composition of the invention must be pharmaceutically acceptable in the sense of being compatible with the compound of formula (I) and the other ingredients of the pharmaceutical composition, and not deleterious to the recipient thereof. It is preferred that the compositions shall not contain any material that may cause an adverse reaction, such as an allergic reaction. The adjuvants, diluents, excipients and carriers that may be used in the pharmaceutical composition of the invention are well known to a person within the art.

As mentioned above, the compositions and particularly pharmaceutical compositions as herein disclosed may, in addition to the compounds herein disclosed, further comprise at least one pharmaceutically acceptable adjuvant, diluent, excipient and/or carrier. In one embodiment the pharmaceutical composition contains neat compound of formula I. In some embodiments, the pharmaceutical compositions comprise from 1 to 99 weight % of said at least one pharmaceutically acceptable adjuvant, diluent, excipient and/or carrier and from 1 to 99 weight % of a compound of formula I as herein disclosed. The combined amount of the active ingredient and of the pharmaceutically acceptable adjuvant, diluent, excipient and/or carrier may not constitute more than 100% by weight (100% w/w) of the composition, particularly the pharmaceutical composition. In accordance with the present invention the pharmaceutical composition may consist of neat compound of formula I (that is 100% w/w compound of formula I) or contain a 1-90% w/w, such as 2-20% w/w, for instance a 3% w/w blend of the compound of formula I or a 10% w/w blend of the compound of formula I. Typically, the 3% w/w blend is a pharmaceutical composition containing 3% w/w compound of formula I and 97% w/w lactose carrier. Typically, the 10% w/w blend is a pharmaceutical composition containing 10% w/w compound of formula I and 90% w/w lactose carrier.

To the person skilled in the art it is well known that particles with a mean mass aerodynamic diameter (MMAD) between 0.1 and 20 μm (micro meter) have an increased probability of depositing in the terminal bronchial and alveolar regions. This particle size range is ideal for many indications in pulmonary drug delivery, since a portion of the material will still deposit in the upper airways as well. (Cf. Controlled Pulmonary Drug Delivery, Smith and Hickey, Editors, Springer 2011, chapter 13).

In accordance with Controlled Pulmonary Drug Delivery, Smith and Hickey, Editors, Springer 2011 in particular chapters 13, 14 and 15 the skilled person will know how to formulate compounds, such as the compound of formula (I) for pulmonary drug delivery.

Dry powder inhalers (DPI), are well known for dispensing medicament to the lungs of a patient. Preferred DPIs for use in the present invention is a monodose dry powder inhaler from Plastiape (HQ, Osnago, Italy), in particular the RS01 Monodose Dry Powder Inhaler.

Current DPI designs include pre-metered and device-metered inhalers, both of which can be driven by patient inspiration alone or with power-assistance of some type. Pre-metered DPIs contain previously measured doses or dose fractions in some type of units (e.g., single or multiple presentations in blisters, capsules, or other cavities) that are subsequently inserted into the device during manufacture or by the patient before use. Thereafter, the dose may be inhaled directly from the pre-metered unit or it may be transferred to a chamber before being inhaled by the patient. Device-metered DPIs have an internal reservoir containing sufficient formulation for multiple doses that are metered by the device itself during actuation by the patient. The wide array of DPI designs, many with characteristics unique to the design, will present challenges in developing information in support of an application. Regardless of the DPI design, the most crucial attributes are the reproducibility of the dose and particle size distribution. Maintaining these qualities through the expiration dating period and ensuring the functionality of the device through its lifetime under patient-use conditions will probably present the most formidable challenge.

Pressurized Metered-Dose Inhalers (pMDI) may also be suitable delivery devices for the present compound of formula (I) and are described in Controlled Pulmonary Drug Delivery, Smith and Hickey, Editors, Springer 2011, chapter 8.

Several types of non-aerosol, breath actuated dry powder inhalers have therefore been provided. For example, U.S. Pat. No. 5,503,144 to Bacon, shows a breath-actuated dry-powder inhaler. The device includes a dry powder reservoir for containing a dry powdered medicament, a metering chamber for removal of the powdered medicament from the reservoir in discrete amounts, and an air inlet for entraining the removed powdered medicament through a mouthpiece upon patient inhalation.

U.S. Pat. No. 5,458,135 discloses a method and apparatus for producing an aerosolized dose of a medicament for subsequent inhalation by a patient. The method comprises first dispersing a preselected amount of the medicament in a predetermined volume of gas, usually air. The dispersion may be formed from a liquid or a dry powder. The method relies on flowing substantially the entire aerosolized dose into a chamber that is initially filled with air and open through a mouthpiece to the ambient. After the aerosolized medicament, has been transferred to the chamber, the patient will inhale the entire dose in a single breath.

U.S. Pat. No. 6,065,472 discloses a powder inhalation device comprising a housing containing a pharmacologically active compound, a conduit with an outlet extending into the housing through which a user can inhale to create an airflow through the conduit, a dosing unit for delivering a dose of the compound to the conduit and baffles arranged within the said conduit to aid disintegration of powder agglomerates entrained in said airflow.

Regardless of whether an aerosol or non-aerosol inhaler is used, it is of utmost importance that particles of the dispensed dry powder medicament be small enough to ensure the adequate penetration of the medicament into the bronchial region of a patient's lungs during inhalation. However, because the dry powder medicament is composed of very small particles, and often provided in a composition including a carrier such as lactose, non-defined agglomerates or aggregates of the medicament form at random prior to being dispensed. It has therefore been found preferably to provide breath-actuated dry powder inhalers with means for breaking down the agglomerates of medicament or medicament and carrier before inhalation of the medicament.

Boehringer Ingelheim provided a new technology in 1997 named Raspimat which is a mechanical nebulizer of the soft mist inhaler type. This mechanical nebulizer is operated by hand without any need for a gas propellant and no need for electrical power. Another mechanical nebulizer is a human powered nebulizer developed by a team from Marquette University. This nebulizer can by operated by an electrical compressor, but it is also suitable for simple mechanical pumps in order to provide a mist into the lungs of patients. Further nebulizers of the electrical type are ultrasonic nebulizers based on the vibrating mesh technology developed by inter alia PARI, Respironics, Omron, Beurer, Aerogen, or ultrasonic nebulizers based on an electronic oscillator that generate a high frequency ultrasonic wave developed by inter alia Omron and Beurer. A further electrical nebulizer is a jet nebulizer also known as atomizers.

In a further embodiment, the nebulizer is selected from a mechanical nebulizer, such as a soft mist inhaler or a human powered nebulizer. In another embodiment, the nebulizer is selected from an electrical nebulizer, such as a nebulizer based on ultrasonic vibrating mesh technology, a jet nebulizer, or an ultrasonic wave nebulizer. Particular suitable nebulizers are based on vibrating mesh technology such as eFlow from PARI. When treating pulmonary fibrosis, in particular IPF, it is important to obtain adequately high local concentrations of the therapeutic in the narrowest parts of the lung tissue, including the bronchioles and the alveoli. Further, it is important that the therapeutic obtains an adequate residence time at the site of action in the lung tissue. However, cough is a central symptom for patients with pulmonary fibrosis and in particular IPF—a symptom that is likely to be aggravated if an irritant is introduced into the lung. However, delivering the compound using a nebulizer, such as an electronic nebulizer, is particularly beneficial, since it allows delivery of the compound to the smallest compartments in the lung, without causing any irritation in the lung. Such relevant nebulizer systems are described in published patent applications US20040089295, US20050056274, US20060054166, US20060097068, US20060102172, US20080060640, US20110155768, and US20120167877, all of which are incorporated herein by reference. Other suitable nebulizers are Tyvaso inhalation system from United Therapeutics, Allera nebulizer system from Gilead, Bronchitol inhaler from Pharmaxis, Diskhaler from GSK, jet and ultrasonic nebulizers from Actelion and Profile Pharma.

Further embodiments of the process are described in the experimental section herein, and each individual process as well as each starting material constitutes embodiments that may form part of embodiments.

The above embodiments should be seen as referring to any one of the aspects (such as 'method for treatment', 'pharmaceutical composition', 'compound for use as a medicament', or 'compound for use in a method') described herein as well as any one of the embodiments described herein unless it is specified that an embodiment relates to a certain aspect or aspects of the present invention.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way.

Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also pro-vide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents.

The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention is further illustrated by the following examples that, however, are not to be construed as limiting the scope of protection. The features disclosed in the foregoing description and in the following examples may, both separately and in any combination thereof, be material for realizing the invention in diverse forms thereof.

Experimental

The current process to manufacture polymorphic Form 1 of 3,3'-Dideoxy-3,3'-bis-[4-(3-fluorophenyl)-1H-1,2,3-triazol-1-yl]-1,1'-sulfanediyl-di-β-D-galactopyranoside involves a final purification step with either trituration or crystallization from ethanol to produce Form 1.

Form 1 of 3,3'-Dideoxy-3,3'-bis-[4-(3-fluorophenyl)-1H-1,2,3-triazol-1-yl]-1,1'-sulfanediyl-di-β-D-galactopyranoside can be prepared via trituration following the steps below:

Suspend crystalline or amorphous 3,3'-Dideoxy-3,3'-bis-[4-(3-fluorophenyl)-1H1,2,3-triazol-1-yl]-1,1'-sulfanediyl-di-β-D-galactopyranoside in ethanol (3.6 vol).
Warm the suspension to 70° C.±5° C.
Stir the mixture for 30 min at 70° C.±5° C.
Allow the mixture to cool to 20° C.±5° C.
Filter and rinse with eight portions of ethanol (8×0.75 vol).
Draw air through the filter cake for a minimum of 15 min.
Dry the filter cake in vacuo at 70° C. with an air bleed to provide purified 3,3'-Dideoxy-3,3'-bis-[4-(3-fluorophenyl)-1H-1,2,3-triazol-1-yl]-1,1'-sulfanediyl-di-β-D-galactopyranoside.

Form 1 of 3,3'-Dideoxy-3,3'-bis-[4-(3-fluorophenyl)-1H-1,2,3-triazol-1-yl]-1,1'-sulfanediyl-di-β-D-galactopyranoside can be prepared via crystallization following the steps below:

Combine crystalline or amorphous 3,3'-Dideoxy-3,3'-bis-[4-(3-fluorophenyl)-1H1,2,3-triazol-1-yl]-1,1'-sulfanediyl-di-β-D-galactopyranoside with ethanol (3.5 vol) and water (1.5 vol).
Heat the mixture to 45-50° C. over 60 to 90 minutes.
Clarify the mixture through a 1 μm filter at 18-23° C.
Adjust the temperature to 30-40° C. (target 38° C.) and concentration the mixture under reduced pressure to about 5 vol.
Add ethanol (10 vol) to the mixture at a temperature of 30-40° C. (target 38° C.).
Re-concentrate the mixture to about 5 vol.
Heat the mixture to 65-75° C. (target 70° C.) and stir for 30-40 minutes.
Cool the mixture to 18-23° C. (target 20° C.) over at least 90 minutes.
Stir the mixture for at least 45 minutes at 18-23° C. (target 20° C.).
Filter and wash the filter cake with ethanol at 18-23° C. (target 20° C.).
Dry the filter cake at 18-23° C. to provide purified 3,3'-Dideoxy-3,3'-bis-[4-(3-fluorophenyl)-1H-1,2,3-triazol-1-yl]-1,1'-sulfanediyl-di-β-D-galactopyranoside.

A polymorph screen was conducted using Form 1 material generated via trituration as the final purification step. The polymorph screen results indicated that there are 6 potential polymorphs for 3,3'-Dideoxy-3,3'-bis-[4-(3-fluorophenyl)-1H-1,2,3-triazol-1-yl]-1,1'-sulfanediyl-di-β-D-galactopyranoside. FIG. 11 includes a table that indicates conditions that generated each polymorph (Form 1-6).

Form 1 is a hydrated form and can be produced from temperature cycling, crash cooling and evaporation experiments in 8 different solvents including methanol, ethanol, acetone, acetonitrile, toluene, tert-butylmethylether, hexane and diisopropylether.

Form 2 is a channel hydrate or hygroscopic form and can be produced from temperature cycling, crash cooling, anti-solvent addition and evaporation experiments in 7 different solvents including acetone, acetone:water (20%), methylethyl ketone, tetrahydrofuran, dichloromethane, dimethylformamide and dimethylacetamide.

Form 3 is a solvate and can be produced from temperature cycling, anti-solvent addition and evaporation in 9 different solvents including dichloromethane, dimethylacetamide, ethyl acetate, isopropyl acetate, methyl isobutyl ketone, tertahydrofuran, acetone, acetone:water (20%) and dimethylacetamide.

Form 4 is a solvate and can be produced from temperature cycling in 2-propanol.

Form 5 is a hydrate and can be produced from temperature cycling in dimethylsulfoxide, water, water:propylene glycol (75:25) and water:PEG400:ethanol (65:25:10).

Form 6 is a hydrate/solvate and can be produced from temperature cycling and evaporation experiments in dimethylformamide and N-methyl-2-pyrrolidone.

3,3'-Dideoxy-3,3'-bis-[4-(3-fluorophenyl)-1H-1,2,3-triazol-1-yl]-1,1'-sulfanediyl-di-β-D-galactopyranoside Form 5 has also been prepared via microfluidization (wet polishing) using water as an anti-solvent.

The amorphous form of 3,3'-Dideoxy-3,3'-bis-[4-(3-fluorophenyl)-1H-1,2,3-triazol-1-yl]-1,1'-sulfanediyl-di-β-D-galactopyranoside has been prepared through spray drying from a solution of acetone:water.

To compare in vitro performance of the different forms for use in inhalation products, an aerodynamic particle size determination (APSD) was performed via New Generation Impactor (NGI) for Form 5 material produced via microfluidization and the amorphous form produced via spray drying. These were compared with the APSD obtained from micronized Form 1 material. For each APSD test, 20 mg 3,3'-Dideoxy-3,3'-bis-[4-(3-fluorophenyl)-1H-1,2,3-triazol-1-yl]-1,1'-sulfanediyl-di-β-D-galactopyranoside was filled into a size 3 HPMC capsule and actuated using a Plastiape Monodose inhaler device. The NGI results are provided in Table 2 and demonstrate that all three forms (Form 1, Form 5 and amorphous) have acceptable in vitro aerosol performance with Fine Particle Fraction (FPF) above 60% and MMAD values in the respirable range.

TABLE 3

APSD Results for Form 1, Form 5 and Amorphous 3,3'-Dideoxy-3,3'-bis-[4-(3-fluorophenyl)-1H-1,2,3-triazol-1-yl]-1,1'-sulfanediyl-di-β-D-galactopyranoside

| Form | Fine Particle Dose (FPD) | Fine - Particle Fraction (FPF) | Mean Mass Aerodynamic Diameter (MMAD) | Geometric Standard Deviation (GSD) |
| --- | --- | --- | --- | --- |
| Form 1 (micronized) | 7.4 mg | 77% | 2.6 μm | 1.8 μm |
| Form 5 (microfluidization) | 7.7 mg | 63% | 2.3 μm | 2.3 μm |
| Amorphous (Spray Drying) | 11.8 mg | 91% | 1.7 μm | 1.8 μm |

Micronized Form 1 was placed on stability under ICH conditions and the results in Table 2A demonstrate that Form 1 is stable both chemically and physically. There is no increase in impurities and both the particle size and crystalline form remain unchanged.

TABLE 3A

| | | | 6 Months | 12 Months |
|---|---|---|---|---|
| Test | Acceptance Criteria | Initial | @ 40° C./75RH | 25° C./60RH |

Stability Results for Micronized Form 1

| Test | Acceptance Criteria | Initial | 6 Months @ 40° C./75RH | 12 Months 25° C./60RH |
|---|---|---|---|---|
| Appearance | White to off-white solid | Conforms | Conforms | Conforms |
| Assay | 95.0-105.0% w/w [1] | 97.9% | 97.2% | 97.7% |
| Specified impurities | DEX283 ≤1% (a/a) | ND | ND | ND |
| | DEX-IMP-284-A ≤1% (a/a) | ND | ND | ND |
| | DEX-IMP-284-B ≤1% (a/a) | 0.90% | 0.89% | 0.89% |
| | DEX-IMP-284-C ≤1% (a/a) | 0.03% | 0.05% | 0.04% |
| Unspecified impurities | ≤1% each (a/a) | 0.922RRT: 0.12% | 0.922RRT: 0.12% | 0.922RRT: 0.12% |
| | | 1.057RRT: 0.08% | 1.057RRT: 0.11% | 1.057RRT: 0.10% |
| | | 1.184RRT: 0.34% | 1.184RRT: 0.34% | 1.184RRT: 0.34% |
| Total Impurities | ≤2.5% (a/a) | 1.54% | 1.57% | 1.54% |
| Water Content | Report result | 4.2% | 5.2% | 4.4% |
| Microbial Limits | TAMC: NMT 100 cfu/g | <10 cfu/g | <10 cfu/g | <10 cfu/g |
| | TYMC: NMT 10 cfu/g | <10 cfu/g | <10 cfu/g | <10 cfu/g |
| | S.aureus: absent in 1 g | absent/g | absent/g | absent/g |
| | P.aeruginosa: absent in 1 g | absent/g | absent/g | absent/g |
| | Bile-tolerant gram-negative bacteria: absent in 1 g | absent/g | absent/g | absent/g |
| Polymorphism | Report Form | Form 1 | Form 1 | Form 1 |

| Test | Acceptance Criteria | Initial | 6 Months @ 40 C./75RH | 12 Months 25° C./60RH |
|---|---|---|---|---|
| Particle Size: | Report results | D10 Results: 0.56 µm | D10 Results: 0.50 µm | D10 Results: 0.51 µm |
| D10 Results | (Target: | D50 Results: 2.37 µm | D50 Results: 1.97 µm | D50 Results: 1.84 µm |
| D50 Results | D50 ~21 µm | D90 Results: 5.09 µm | D90 Results: 4.68 µm | D90 Results: 4.29 µm |
| D90 Results | D90 ≤5 µm) | | | |

Figure 8:
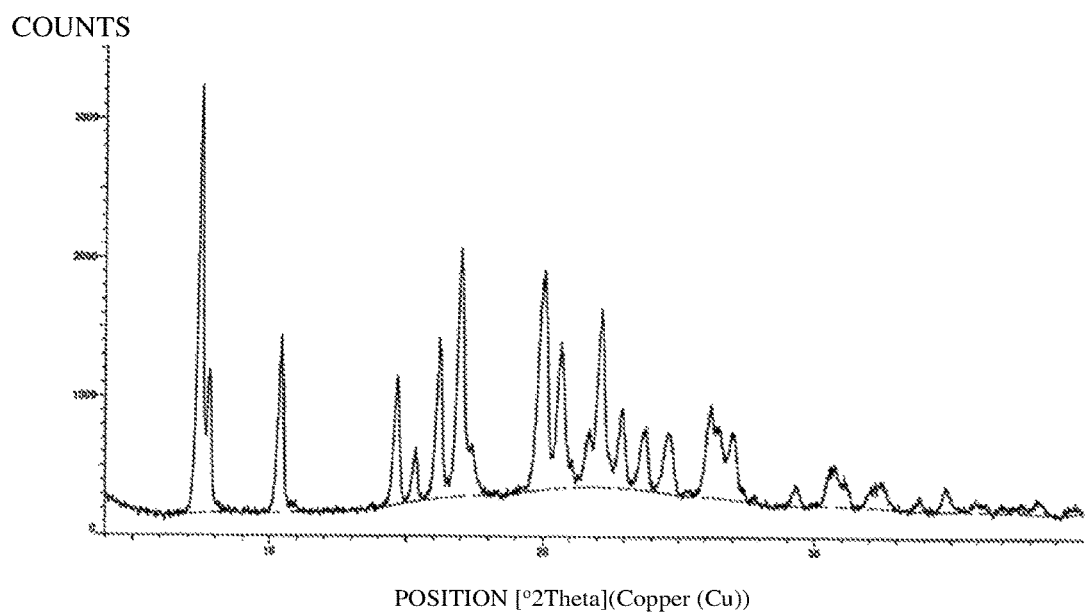
FIG. 8: XRPD Diffractogram for micronized form 1.
Figure 9:
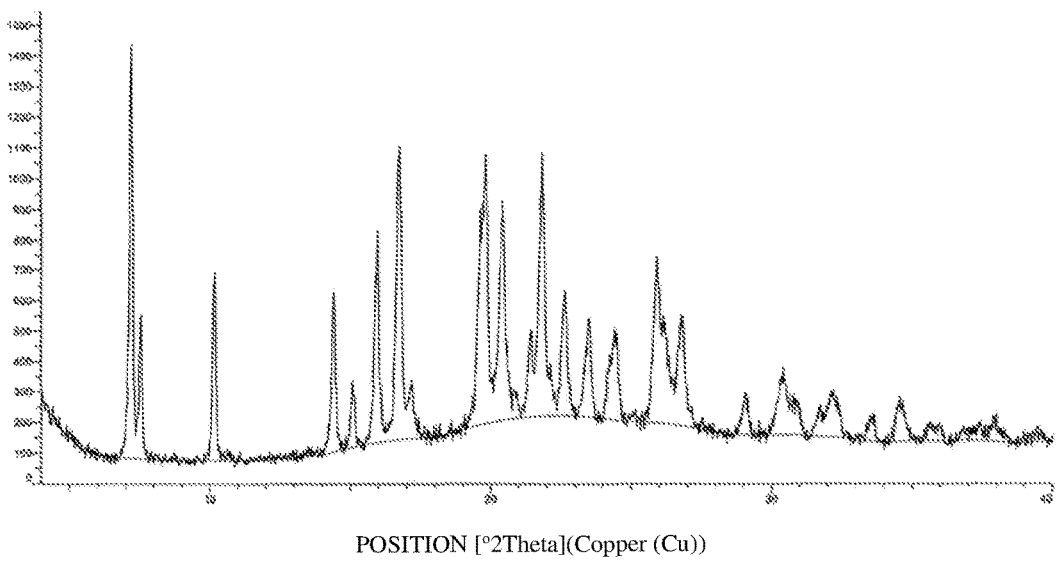
FIG. 9: XRPD Diffractogram for micronized form 1.
Figure 10:
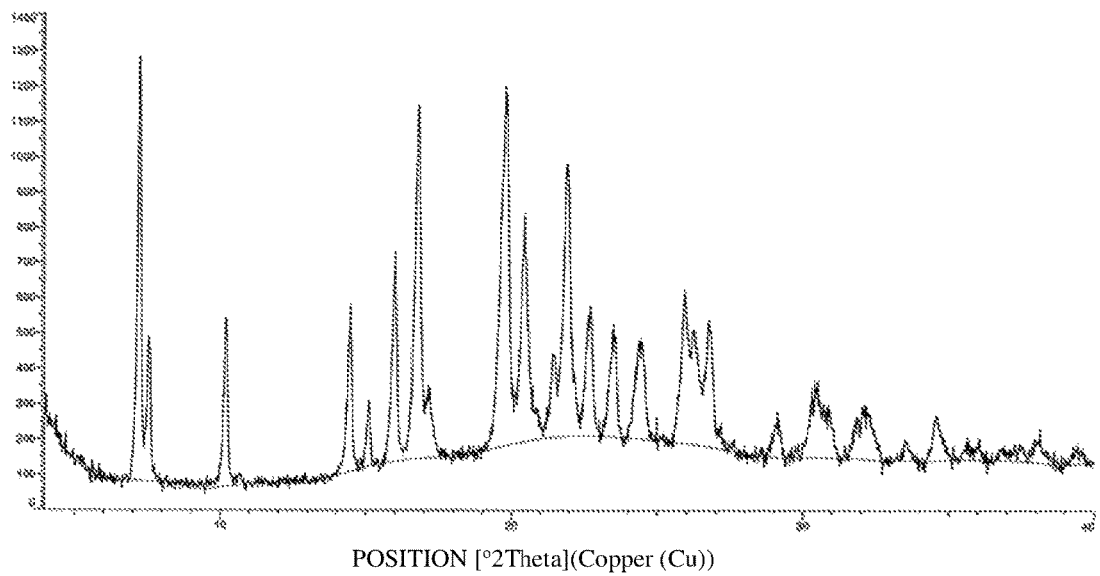
FIG. 10: XRPD Diffractogram for micronized form 1.

FIG. 8 shows XRPD scan at Initial time point.
FIG. 9 shows XRPD scan at 6 Months at 40° C./75 RH.
FIG. 10 shows XRPD scan at 12 Months at 25° C./60 RH.

EXAMPLES

Preparation of Form 1

3 mL of methanol was added to 300 mg of 3,3'-Dideoxy-3,3'-bis-[4-(3-fluorophenyl)-1H1,2,3-triazol-1-yl]-1,1'-sulfanediyl-di-β-D-galactopyranoside (e.g. amorphous form) or alternately 900 ul methanol was added to 100 mg 3,3'-Dideoxy-3,3'-bis-[4-(3-fluorophenyl)-1H1,2,3-triazol-1-yl]-1,1'-sulfanediyl-di-β-D-galactopyranoside (e.g. amorphous form) to form a slurry. The slurry was temperature cycled between room temperature (RT) and 40° C. (4 hour cycles) for about 6 or 7 days. The sample was filtered and allowed to dry at ambient followed by about 2 hours drying under vacuum.

Form 1 has been shown to have suitable characteristics that justifies its use in a dry powder inhaler (DPI).

Preparation of Form 2

3 mL of acetone:water (20%) was added to 300 mg of 3,3'-Dideoxy-3,3'-bis-[4-(3-fluorophenyl)-1H-1,2,3-triazol-1-yl]-1,1'-sulfanediyl-di-β-D-galactopyranoside (e.g. amorphous form) or alternately 300 ul acetone:water (20%) was added to 100 mg 3,3'-Dideoxy-3,3'-bis[4-(3-fluorophenyl)-1H-1,2,3-triazol-1-yl]-1,1'-sulfanediyl-di-β-D-galactopyranoside (e.g. amorphous form) to form a slurry. The slurry was temperature cycled between RT and 40° C. (4 hour cycles) for about 6-7 days. The sample was filtered and allowed to dry at ambient followed by about 2 hours drying under vacuum.

Preparation of Form 3

2.5 mL of methyl isobutyl ketone (MIBK) was added to 300 mg of 3,3'-Dideoxy-3,3'-bis-[4-(3-fluorophenyl)-1H-1,2,3-triazol-1-yl]-1,1'-sulfanediyl-di-β-D-galactopyranoside (e.g. amorphous form) or alternately 900 ul of MIBK was added to 100 mg of 3,3'-Dideoxy-3,3'-bis-[4-(3-fluorophenyl)-1H-1,2,3-triazol-1-yl]-1,1'-sulfanediyl-di-β-D-galactopyranoside (e.g. amorphous form) to form a slurry. The slurry was temperature cycled between RT and 40° C. (4 hour cycles) for about 6-7 days. The sample was filtered and allowed to dry at ambient followed by about 2-3 hours drying under vacuum.

Preparation of Form 4

2 mL of 2-propanol was added to 300 mg of 3,3'-Dideoxy-3,3'-bis-[4-(3-fluorophenyl)-1H1,2,3-triazol-1-yl]-1,1'-sulfanediyl-di-β-D-galactopyranoside (e.g. amorphous form) or alternately 500 ul of 2-propanol was added to 100 mg 3,3'-Dideoxy-3,3'-bis-[4-(3-fluorophenyl)-1H-1,2,3-triazol-1-yl]-1,1'-sulfanediyl-di-β-D-galactopyranoside (e.g. amorphous form) to form a slurry. The slurry was temperature cycled between RT and 40° C. (4 hour cycles) for about 6-7 days. The sample was filtered and allowed to dry at ambient followed by about 2-3 hours drying under vacuum.

Preparation of Form 5

2.5 mL of water was added to 300 mg of 3,3'-Dideoxy-3,3'-bis-[4-(3-fluorophenyl)-1H-1,2,3-triazol-1-yl]-1,1'-sulfanediyl-di-β-D-galactopyranoside (e.g. amorphous form) or alternately 800 ul water was added to 100 mg 3,3'-Dideoxy-3,3'-bis-[4-(3-fluorophenyl)-1H-1,2,3-triazol-1-yl]-1,1'-sulfanediyl-di-β-D-galactopyranoside (e.g. amorphous form) to form a slurry. The slurry was temperature cycled between RT and 40° C. (4 hour cycles) for about 6-7 days. The sample was filtered and allowed to dry at ambient followed by about 2-3 hours drying under vacuum.

Form 5 can also be prepared by microfluidization to produce material with a particle size in the respirable range. 10 g of 3,3'-Dideoxy-3,3'-bis-[4-(3-fluorophenyl)-1H-1,2,3-triazol-1-yl]-1,1'-sulfanediyl-di-β-D-galactopyranoside (e.g. amorphous form) was suspended in 190 g water. The suspension was processed using a Microfluidics High Pressure Homogenizer equipped with a 200 μm auxiliary processing module and a 100 μm interaction chamber. The unit was operated at a pressure of approximately 750 bar. As a final step, the material was spray dried to isolate the dried Form 5 material.

Form 5 is stable and is particularly suitable for administration by a nebulizer.

Preparation of Form 6

1 mL of dimethylformamide (DMF) was added to 300 mg of 3,3'-Dideoxy-3,3'-bis-[4-(3-fluorophenyl)-1H-1,2,3-triazol-1-yl]-1,1'-sulfanediyl-di-β-D-galactopyranoside (e.g. amorphous form) or alternately 200 ul DMF was added to 100 mg 3,3'-Dideoxy-3,3'-bis-[4-(3-fluorophenyl)-1H-1,2,3-triazol-1-yl]-1,1'-sulfanediyl-di-β-D-galactopyranoside (e.g. amorphous form) to form a slurry. The slurry was temperature cycled between RT and 40° C. (4 hour cycles) for about 0.5-1 day. The sample formed a solution and was allowed to evaporate. The sample was dried for ca. 2 hours under vacuum. Alternately, once precipitation of was observed during the evaporation step, the sample was temperature cycled for a further about 1 day and dried for about 1 day under vacuum.

Preparation of Amorphous

Table 3 provides an example of spray-drying conditions used to prepare amorphous 3,3'-Dideoxy-3,3'-bis-[4-(3-fluorophenyl)-1H-1,2,3-triazol-1-yl]-1,1'-sulfanediyl-di-β-D-galactopyranoside. Alternately, the spray-drying solvent can have other proportions of acetone:water from 50:50 to 80:20.

TABLE 4

Spray-Drying Conditions for Amorphous 3,3'-Dideoxy-3,3'-bis[4-(3-fluorophenyl)-1H-1,2,3-triazol-1-yl]-1,1'-sulfanediyl-di-β-D-galactopyranoside (API)

| Solvent | Acetone: Water (50:50)-250 mL |
|---|---|
| API | 8.0 g |
| Feed Concentration | 3.5% wt/wt |
| Relative saturation of the drying gas at the outlet of the drying chamber | 1.4/0.1% |
| Flowrate of feed to spray dryer | 5 ml/min |
| Rotameter | 60 mm |
| Drying gas temperature at inlet to drying chamber | 144° C. |
| Drying gas temperature at outlet of drying chamber | 75° C. |
| Temperature at exit of condenser | 5° C. |
| Drying time | 50 min |

We claim:

1. A polymorph of a compound of formula (I)

I 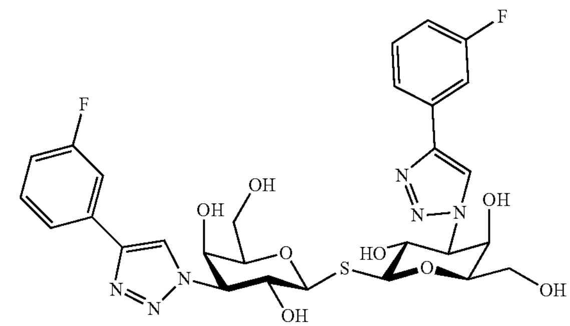 wherein the polymorph is 3,3'-Dideoxy-3,3'-bis-[4-(3-fluorophenyl)-1H-1,2,3-triazol-1-yl]-1,1'-sulfanediyl-di-β-D-galactopyranoside and wherein:

the polymorph has a polymorphic form selected from the group consisting of a polymorphic form 2 as identified in the XRPD diffractogram in FIG. 3, a polymorphic form 3 as identified in the XRPD diffractogram in FIG. 4, a polymorphic form 4 as identified in the XRPD diffractogram in FIG. 5, a polymorphic form 5 as identified in the XRPD diffractogram in FIG. 6, and a polymorphic form 6 as identified in the XRPD diffractogram in FIG. 7.

2. The polymorph of claim 1 wherein the compound of formula (I) is 3,3'-Dideoxy-3,3'-bis-[4-(3-fluorophenyl)-1H-1,2,3-triazol-1-yl]-1,1'-sulfanediyl-di-β-D-galactopyranoside as a hydrate and the polymorphic form is selected from the group consisting of polymorphic form 2, polymorphic form 5, and polymorphic form 6.

3. The polymorph of claim 2 wherein the 3,3'-Dideoxy-3,3'-bis-[4-(3-fluorophenyl)-1H-1,2,3-triazol-1-yl]-1,1'-sulfanediyl-di-β-D-galactopyranoside hydrate contains 3-5% water (weight %).

4. The polymorph of claim 1 wherein the polymorph is micronized.

5. The polymorph of claim 4 wherein the polymorph is micronized to a size that can reach the bronchioles and/or the alveoli of the human.

6. A pharmaceutical composition comprising the polymorph of claim 1, and optionally a pharmaceutically acceptable additive.

7. A process of making a polymorph of claim 1 comprising the steps of suspending or dissolving 3,3'-Dideoxy-3,3'-bis-[4-(3-fluorophenyl)-1H-1,2,3-triazol-1-yl]-1,1'-sulfanediyl-di-β-D-galactopyranoside in an organic solvent and then making the polymorph by temperature cycling, crash cooling, anti-solvent addition, evaporation, or a combination thereof.

8. A method for treatment of pulmonary fibrosis in a human comprising administering to the lung tissue of the human an amount of the polymorph of claim 1 effective to treat said pulmonary fibrosis.

9. The method of claim 1 wherein the administration is carried out by a dry powder inhaler.

10. The method of claim 9 wherein the administration is carried out by a monodose dry powder inhaler.

11. The method of claim 8 wherein the polymorph is administered to the bronchioles and/or the alveoli of the human.

12. The method of claim 8 wherein the amount is a once daily amount from 0.15 mg to 50 mg.

13. The method of claim 12, wherein the amount is a once daily amount selected from the group consisting of: 0.15 mg to 0.50 mg, 0.50 mg to 0.75 mg, 0.75 mg to 1.25 mg, 1.25 mg to 1.5 mg, 1.5 mg to 1.75 mg, 1.75 mg to 2 mg, 2 mg to 2.25 mg, 2.25 mg to 2.5 mg, 2.5 mg to 2.75 mg, 2.75 mg to 3 mg, 3 mg to 5 mg, 5 mg to 7 mg, 7 mg to 8 mg, 8 mg to 10 mg, 10 mg to 20 mg and 20 mg to 50 mg.

14. A method for treatment of pulmonary fibrosis in a human comprising administering to the lung tissue of the human an amount of the polymorph of claim 2 effective to treat said pulmonary fibrosis.

15. A method for treatment of pulmonary fibrosis in a human comprising administering to the lung tissue of the human an amount of the polymorph of claim 3 effective to treat said pulmonary fibrosis.

16. A method for treatment of pulmonary fibrosis in a human comprising administering to the lung tissue of the human an amount of the polymorph of claim 4 effective to treat said pulmonary fibrosis.

\* \* \* \* \*